(12) United States Patent
Dunn et al.

(10) Patent No.: US 8,647,587 B2
(45) Date of Patent: *Feb. 11, 2014

(54) POWDER DISPENSING ASSEMBLY FOR A WASTE CONTAINER

(75) Inventors: Steven B. Dunn, Beverly Hills, PA (US); Mark A. Hatherill, Beverly Hills, CA (US); Kevin D. Johnson, Tarzana, CA (US)

(73) Assignee: Munchkin, Inc, Van Nuys, CA (US)

( * ) Notice: Subject to any disclaimer, the term of this patent is extended or adjusted under 35 U.S.C. 154(b) by 956 days.

This patent is subject to a terminal disclaimer.

(21) Appl. No.: 12/609,140

(22) Filed: Oct. 30, 2009

(65) Prior Publication Data

US 2011/0104022 A1    May 5, 2011

(51) Int. Cl.
| A61L 2/00 | (2006.01) |
| B65D 25/00 | (2006.01) |
| A61L 9/04 | (2006.01) |
| A24F 25/00 | (2006.01) |
| B05B 1/32 | (2006.01) |
| B67D 5/64 | (2006.01) |

(52) U.S. Cl.
USPC .......... 422/261; 422/292; 422/300; 220/87.1; 220/522; 220/402; 239/6; 239/59; 239/457; 222/166

(58) Field of Classification Search
USPC ............. 422/1, 5, 28, 32, 122, 261, 292, 300; 220/87.1, 522, 402; 55/316, 385.4; 239/6, 59, 457; 222/166
See application file for complete search history.

(56) References Cited

U.S. PATENT DOCUMENTS

| 1,633 | A | 6/1840 | Sellers et al. |
| 18,046 | A | 8/1857 | Hinckley |

(Continued)

FOREIGN PATENT DOCUMENTS

| DE | 202005015117 | 2/2007 |
| EP | 0913344 A1 | 5/1999 |

(Continued)

OTHER PUBLICATIONS

International Search Report & Written Opinion Dated Jul. 28, 2011. Korean Intellectual Property Office is the ISA.

(Continued)

Primary Examiner — Monzer R Chorbaji
(74) Attorney, Agent, or Firm — Robert Z. Evora, Esq.

(57) ABSTRACT

A powder dispenser for a waste disposal system includes a mounting portion that is adapted to be secured to a waste disposal unit, and a container defining an interior space in which a powder such as sodium bicarbonate may be stored. The container is releasably mounted to the underside of a hinged lid member of the waste disposal unit. A directional dispensing system is provided for dispensing powder from the container into a targeted portion of the waste disposal system. The directional dispensing system is constructed and arranged to concentrate initial dispersal of the powder to a single side of the container and includes a dispensing orifice. The dispensing orifice is preferably oriented to limit initial dispersal of the powder within a defined angular range with respect to the longitudinal axis of the lid member, and is spaced axially and laterally with respect to the waste disposal unit at distances that facilitate distribution of the powder to desired targeted portions of the waste disposal unit. The container and waste disposal unit also define a venting path so that the powder within the container can also absorb odors within the waste disposal unit.

25 Claims, 7 Drawing Sheets

(56) References Cited

U.S. PATENT DOCUMENTS

| | | | |
|---|---|---|---|
| 111,521 A | 2/1871 | Dodge | |
| 293,459 A | 2/1884 | Hawn | |
| 428,228 A | 5/1890 | Price | |
| 459,875 A | 9/1891 | Locke | |
| 471,433 A | 3/1892 | Rice | |
| 503,113 A | 8/1893 | Osterloh | |
| 627,434 A | 6/1899 | Miller | |
| 685,179 A | 10/1901 | Seebers | |
| 772,538 A * | 10/1904 | Walters | 76/38 |
| 859,497 A | 7/1907 | Hood | |
| 860,183 A | 7/1907 | Barr | |
| 1,719,185 A | 7/1929 | Lowy | |
| 2,015,824 A * | 10/1935 | Trompeter | 220/87.1 |
| 2,067,547 A | 1/1937 | Schneider et al. | |
| 2,271,918 A | 2/1942 | Glowka | |
| 2,352,503 A | 6/1944 | Walton | |
| 2,610,432 A | 9/1952 | Ambrose | |
| 3,086,674 A | 4/1963 | Scheuerman | |
| 3,214,065 A | 10/1965 | Thornton | |
| 3,310,224 A | 3/1967 | Laguerre | |
| 3,536,192 A | 10/1970 | Couper | |
| 3,619,822 A | 11/1971 | Carmichael | |
| 3,772,712 A | 11/1973 | Renn et al. | |
| 3,779,157 A | 12/1973 | Ross, Jr. et al. | |
| 3,908,336 A | 9/1975 | Forslund | |
| 3,959,947 A | 6/1976 | Sonnino | |
| 4,162,602 A | 7/1979 | Achelpohl et al. | |
| 4,175,603 A | 11/1979 | Iaboni et al. | |
| 4,303,710 A | 12/1981 | Bullard et al. | |
| 4,349,123 A | 9/1982 | Yang | |
| 4,427,110 A * | 1/1984 | Shaw, Jr. | 206/205 |
| 4,437,575 A | 3/1984 | Hahn | |
| D274,462 S | 6/1984 | Rakocy et al. | |
| 4,561,563 A | 12/1985 | Woods | |
| 4,617,230 A | 10/1986 | Shah et al. | |
| 4,637,061 A | 1/1987 | Riese | |
| 4,687,711 A | 8/1987 | Vietto et al. | |
| 4,724,185 A | 2/1988 | Shah | |
| 4,760,784 A | 8/1988 | Whiteside | |
| 4,868,024 A | 9/1989 | Cross et al. | |
| 4,869,049 A | 9/1989 | Richards et al. | |
| 4,880,852 A | 11/1989 | Hoshino et al. | |
| 4,890,934 A | 1/1990 | Feaver et al. | |
| 4,906,495 A | 3/1990 | Martini et al. | |
| 4,934,529 A | 6/1990 | Richards et al. | |
| 4,946,720 A | 8/1990 | Oishi et al. | |
| 4,948,266 A | 8/1990 | Bencic | |
| 4,948,639 A | 8/1990 | Brooker et al. | |
| 4,957,518 A | 9/1990 | Brassell | |
| 4,983,171 A | 1/1991 | Schirmer | |
| 4,996,727 A | 3/1991 | Wyatt | |
| 5,022,553 A | 6/1991 | Pontius | |
| 5,056,293 A | 10/1991 | Richards et al. | |
| 5,116,139 A | 5/1992 | Young et al. | |
| 5,120,454 A | 6/1992 | Wieties | |
| 5,125,526 A | 6/1992 | Sumanis | |
| 5,129,735 A | 7/1992 | Neal et al. | |
| 5,147,055 A | 9/1992 | Samson et al. | |
| 5,158,199 A | 10/1992 | Pontius | |
| 5,174,462 A | 12/1992 | Hames | |
| 5,183,157 A | 2/1993 | Darden | |
| 5,184,575 A | 2/1993 | Reinartz | |
| D334,975 S | 4/1993 | Bunce et al. | |
| 5,222,620 A | 6/1993 | Lima et al. | |
| 5,278,282 A | 1/1994 | Nauman et al. | |
| 5,294,017 A | 3/1994 | Li | |
| 5,382,631 A | 1/1995 | Stehling et al. | |
| 5,385,259 A | 1/1995 | Bernstein et al. | |
| 5,391,423 A | 2/1995 | Wnuk et al. | |
| 5,405,041 A | 4/1995 | Van Brackle | |
| 5,520,303 A | 5/1996 | Bernstein et al. | |
| 5,535,913 A | 7/1996 | Asbach et al. | |
| 5,582,820 A | 12/1996 | Yamamoto et al. | |
| 5,590,512 A | 1/1997 | Richards et al. | |
| 5,637,366 A | 6/1997 | Davis et al. | |
| D380,538 S | 7/1997 | Muller et al. | |
| 5,642,810 A | 7/1997 | Warner et al. | |
| 5,651,231 A | 7/1997 | Garland | |
| 5,655,680 A | 8/1997 | Asbach et al. | |
| D383,864 S | 9/1997 | Billings | |
| 5,671,847 A | 9/1997 | Pedersen et al. | |
| 5,692,837 A | 12/1997 | Beer | |
| 5,752,658 A | 5/1998 | Gibbs et al. | |
| 5,759,648 A | 6/1998 | Idlas | |
| 5,762,421 A | 6/1998 | Ross | |
| 5,765,339 A | 6/1998 | Garland | |
| 5,799,909 A | 9/1998 | Ziegler | |
| 5,813,200 A | 9/1998 | Jacoby et al. | |
| 5,852,114 A | 12/1998 | Loomis et al. | |
| 5,884,556 A | 3/1999 | Klepacki et al. | |
| 5,886,078 A | 3/1999 | Sullivan et al. | |
| 5,897,084 A | 4/1999 | Judge | |
| 5,962,598 A | 10/1999 | Mack et al. | |
| 5,988,520 A | 11/1999 | Bitner | |
| 6,000,323 A | 12/1999 | Schlegel | |
| 6,007,030 A | 12/1999 | Judge | |
| D424,677 S | 5/2000 | Chen | |
| 6,065,272 A | 5/2000 | Lecomte | |
| 6,071,451 A | 6/2000 | Wang et al. | |
| 6,096,420 A | 8/2000 | Wilhoit et al. | |
| 6,116,780 A | 9/2000 | Young et al. | |
| 6,120,743 A | 9/2000 | Papari | |
| D432,224 S | 10/2000 | Hautmann et al. | |
| 6,128,890 A | 10/2000 | Firth | |
| 6,129,716 A | 10/2000 | Steer | |
| 6,141,945 A | 11/2000 | Becher | |
| 6,147,167 A | 11/2000 | Mack et al. | |
| 6,164,442 A | 12/2000 | Stravitz | |
| 6,164,821 A | 12/2000 | Randall | |
| 6,170,240 B1 | 1/2001 | Jacoby et al. | |
| 6,174,990 B1 | 1/2001 | Noda | |
| 6,199,220 B1 | 3/2001 | Smith | |
| 6,202,877 B1 | 3/2001 | La Torre et al. | |
| 6,258,423 B1 | 7/2001 | Giori | |
| 6,296,388 B1 | 10/2001 | Galomb et al. | |
| 6,303,220 B1 | 10/2001 | Minamoto | |
| 6,316,067 B1 | 11/2001 | Edwards et al. | |
| 6,345,911 B1 | 2/2002 | Young et al. | |
| 6,354,062 B1 | 3/2002 | Haughton et al. | |
| D455,485 S | 4/2002 | Hensel | |
| 6,370,847 B1 | 4/2002 | Jensen et al. | |
| D458,359 S | 6/2002 | Blanchette | |
| 6,453,640 B1 | 9/2002 | Hayashi | |
| 6,494,619 B1 | 12/2002 | Sulpizio | |
| 6,516,588 B2 | 2/2003 | Jensen et al. | |
| 6,532,605 B1 | 3/2003 | Howell | |
| 6,540,103 B2 | 4/2003 | Silvers | |
| D475,444 S | 6/2003 | Laferriere et al. | |
| 6,585,153 B2 | 7/2003 | Ryan | |
| 6,596,814 B2 | 7/2003 | Kim et al. | |
| 6,612,099 B2 | 9/2003 | Stravitz | |
| D482,109 S | 11/2003 | Woods | |
| D482,110 S | 11/2003 | Laferriere et al. | |
| D482,111 S | 11/2003 | Laferriere et al. | |
| 6,719,194 B2 | 4/2004 | Richards | |
| 6,722,107 B2 | 4/2004 | Morand | |
| D491,257 S | 6/2004 | Picken, Jr. | |
| D492,018 S | 6/2004 | Schröder | |
| 6,804,930 B2 | 10/2004 | Stravitz | |
| 6,817,164 B2 | 11/2004 | Mauffette et al. | |
| D500,590 S | 1/2005 | Sachen | |
| D501,602 S | 2/2005 | Karlsson et al. | |
| 6,851,251 B2 | 2/2005 | Stravitz | |
| 6,894,085 B2 | 5/2005 | Beaverson et al. | |
| 6,901,974 B2 | 6/2005 | Chomik et al. | |
| 6,914,091 B2 | 7/2005 | Donald et al. | |
| 6,921,581 B2 | 7/2005 | Van Gelder et al. | |
| 6,925,781 B1 | 8/2005 | Knuth et al. | |
| 6,931,684 B1 | 8/2005 | Henegar | |
| 6,941,733 B2 | 9/2005 | Chomik et al. | |
| 6,956,088 B2 | 10/2005 | Farley et al. | |
| 6,974,029 B2 | 12/2005 | Morand et al. | |
| D515,683 S | 2/2006 | LaBlaine | |
| 6,993,891 B2 | 2/2006 | Richardson et al. | |

(56) References Cited

U.S. PATENT DOCUMENTS

| | | |
|---|---|---|
| 6,994,247 B2 | 2/2006 | Richards |
| D517,673 S | 3/2006 | Yamamoto et al. |
| D523,632 S | 6/2006 | Handley |
| 7,073,311 B2 | 7/2006 | Chomik et al. |
| 7,086,569 B2 * | 8/2006 | Stravitz ................ 222/157 |
| 7,100,767 B2 | 9/2006 | Chomik et al. |
| 7,114,314 B2 | 10/2006 | Stravitz |
| 7,114,534 B2 | 10/2006 | Chomik et al. |
| 7,146,785 B2 | 12/2006 | Stravitz |
| 7,168,591 B1 | 1/2007 | Miller |
| 7,175,918 B2 | 2/2007 | Saraf et al. |
| 7,178,314 B2 | 2/2007 | Chomik et al. |
| 7,241,493 B2 | 7/2007 | Zhou |
| D550,345 S | 9/2007 | Weggelaar |
| D551,333 S | 9/2007 | Wu |
| 7,279,198 B1 | 10/2007 | Knauf |
| 7,288,593 B2 | 10/2007 | Yang et al. |
| 7,300,207 B2 | 11/2007 | Linneweil |
| 7,316,100 B2 | 1/2008 | Stravitz |
| 7,328,547 B2 | 2/2008 | Mehta et al. |
| 7,347,624 B2 | 3/2008 | Savicki, Sr. |
| D565,715 S | 4/2008 | Wu |
| 7,350,663 B2 | 4/2008 | Chomik et al. |
| 7,377,203 B2 | 5/2008 | Chomik |
| 7,434,377 B2 | 10/2008 | Stravitz et al. |
| 7,459,191 B2 | 12/2008 | Sleight et al. |
| D585,129 S | 1/2009 | Huang |
| 7,490,734 B2 | 2/2009 | Carr |
| 7,500,339 B2 | 3/2009 | Knuth et al. |
| 7,503,152 B2 | 3/2009 | Stravitz et al. |
| 7,503,159 B2 | 3/2009 | Stravitz et al. |
| D591,415 S | 4/2009 | Wu |
| D591,509 S | 5/2009 | Lown et al. |
| 7,629,036 B2 | 12/2009 | Chomik et al. |
| D609,008 S | 2/2010 | Diamant |
| 7,712,285 B2 | 5/2010 | Stravitz et al. |
| 2001/0037627 A1 | 11/2001 | Hausslein |
| 2002/0162304 A1 | 11/2002 | Stravitz |
| 2003/0078552 A1 | 4/2003 | Tepper et al. |
| 2003/0190097 A1 | 10/2003 | Hajianpour |
| 2004/0083681 A1 | 5/2004 | Stravitz |
| 2004/0191438 A1 | 9/2004 | Cosentino et al. |
| 2005/0033259 A1 | 2/2005 | Stravitz |
| 2005/0044819 A1 | 3/2005 | Chomik et al. |
| 2005/0079372 A1 | 4/2005 | Schmal et al. |
| 2005/0183400 A1 | 8/2005 | Stravitz et al. |
| 2005/0188661 A1 | 9/2005 | Stravitz et al. |
| 2005/0193691 A1 | 9/2005 | Stravitz et al. |
| 2005/0193692 A1 | 9/2005 | Stravitz et al. |
| 2005/0217214 A1 | 10/2005 | Richardson et al. |
| 2005/0228354 A1 | 10/2005 | Scholer |
| 2005/0274093 A1 | 12/2005 | Stravitz et al. |
| 2006/0013512 A1 | 1/2006 | Shaw |
| 2006/0021301 A1 | 2/2006 | Stravitz et al. |
| 2006/0130438 A1 | 6/2006 | Stravitz et al. |
| 2006/0130439 A1 | 6/2006 | Stravitz et al. |
| 2006/0237461 A1 | 10/2006 | Chomik et al. |
| 2006/0249418 A1 | 11/2006 | Chomik et al. |
| 2006/0251842 A1 | 11/2006 | Chomik et al. |
| 2007/0045324 A1 | 3/2007 | Mitchell et al. |
| 2007/0053616 A1 | 3/2007 | Plouff |
| 2007/0157581 A1 | 7/2007 | Webb et al. |
| 2007/0175182 A1 | 8/2007 | Stravitz et al. |
| 2007/0180798 A1 | 8/2007 | Stravitz et al. |
| 2007/0189643 A1 | 8/2007 | Tresenfeld |
| 2007/0246465 A1 | 10/2007 | Stravitz et al. |
| 2008/0019618 A1 | 1/2008 | Dayton et al. |
| 2008/0134644 A1 | 6/2008 | Knuth et al. |
| 2008/0179330 A1 | 7/2008 | Brooks et al. |
| 2008/0199643 A1 | 8/2008 | Withers |
| 2008/0247679 A1 | 10/2008 | Dayton et al. |
| 2008/0310772 A1 | 12/2008 | Dayton et al. |
| 2009/0065521 A1 | 3/2009 | Amundson et al. |
| 2011/0099942 A1 * | 5/2011 | Dunn et al. .......... 53/111 RC |

FOREIGN PATENT DOCUMENTS

| | | |
|---|---|---|
| GB | 099031 | 9/1933 |
| GB | 772538 | 4/1957 |
| GB | 2206094 | 12/1988 |
| JP | 3019134 | 9/1995 |
| JP | 11319048 | 11/1999 |
| JP | 2004175508 | 6/2004 |
| JP | 3134078 | 7/2007 |
| WO | 99/39675 | 8/1999 |
| WO | 02/42364 | 5/2002 |
| WO | 02/051788 | 7/2002 |
| WO | 2005/042381 | 5/2005 |
| WO | 2005042381 A2 | 5/2005 |
| WO | 2007/130889 | 11/2007 |
| WO | 2007130889 A2 | 11/2007 |
| WO | 2008/059282 | 5/2008 |

OTHER PUBLICATIONS

Copending U.S. Appl. No. 12/172,715, filed Jul. 14, 2008 entitled "Waste Disposal Devices".

Copending U.S. Appl. No. 12/172,758, filed Jul. 14, 2008 entitled "Tubing Assembly for Waste Disposal Devices".

Copending U.S. Appl. No. 12/172,793, filed Jul. 14, 2008 entitled "Waste Disposal Devices".

* cited by examiner

POWDER DISPENSING ASSEMBLY FOR A WASTE CONTAINER

BACKGROUND OF THE INVENTION

1. Field of the Invention

This invention relates generally to waste disposal systems, such as trash cans and diaper pails, for household and institutional use. More specifically, this invention pertains to an improved waste disposal system and a powder dispensing assembly for dispensing a deodorizing or odor-absorbing powder such as sodium bicarbonate into a targeted area of a waste disposal system.

2. Description of the Related Technology

Conventional deodorizing techniques for waste disposal systems such as trash cans and diaper pails include periodically spraying the inside of the container with an aerosol deodorant, or using a liner or disposable bag that has been treated or impregnated with a substance that is intended to suppress or mask odors.

U.S. Pat. No. 7,086,569 to Stravitz describes an odor control assembly for such systems in which a deodorizing powder is provided in a cartridge that is secured to an underside of a hinged lid of a trash container. The cartridge is provided with a plurality of dispensing openings in the bottom of the cartridge that are oriented to disperse the powder downwardly and substantially evenly in all directions when the lid is in the closed position.

Unfortunately, the present inventors have found that such a dispensing orientation does not optimally disperse the powder into the desired areas of the waste container when the lid is open and closed. Instead, powder that falls from the container when the lid is open will tend to fall disproportionately on the side of the container that bears the hinge. When the lid is open to the extent that it is close to being perpendicular to the closed position, powder will even tend to fall directly on the hinge or the rim of the trash container. This wastes the powder, can cause malfunction of mechanical components of the waste container and can also create a mess on the surrounding floor or carpet.

In addition, conventional powder dispensers for waste disposal systems typically did not provide precise metering of the powder material that would ensure that an efficacious amount of powder material is dispensed each time a lid of the waste container is opened and closed, and that would conserve the powder material to ensure an optimal number of lid opening and closing cycles can be accommodated before the powder dispenser needs to be replaced or refilled.

A need exists for an improved system and method for dispensing a deodorizing or odor-absorbing powder in a waste disposal system that optimally disperses the powder to the desired portions of the waste disposal system whether the lid is open or closed, and that efficaciously meters the powder material into the waste disposal system.

SUMMARY OF THE INVENTION

Accordingly, it is an object of the invention to provide an improved system and method for dispensing a deodorizing or odor-absorbing powder in a waste disposal system that optimally disperses the powder to the desired portions of the waste disposal system whether the lid is open or closed, and that efficaciously meters the powder material into the waste disposal system.

In order to achieve the above and other objects of the invention, a powder dispenser for a waste disposal unit according to a first aspect of the invention includes a mounting portion that is adapted to be secured to a waste disposal unit; a container defining an interior space in which a powder may be stored, the container having a longitudinal axis; and a directional dispensing portion for dispensing powder from the container into a targeted portion of the waste disposal unit. The directional dispensing portion is constructed and arranged to concentrate dispersal of the powder to a single side of the container and within an angular range of substantially about 40° to about 80° with respect to the longitudinal axis.

According to a second aspect of the invention, a waste disposal system includes a housing and a lid member that is mounted to the housing by a hinge. The lid member has a longitudinal axis that is substantially vertical when the lid is in a closed position. A powder dispensing unit is mounted to an underside of the lid. The powder dispensing unit includes a container that defines an interior space in which a powder may be stored, and a directional dispensing portion for dispensing powder from the container into a targeted portion of the waste disposal unit. The directional dispensing portion is constructed and arranged to concentrate dispersal of the powder to a single side of the container and within an angular range of substantially about 40° to about 80° with respect to the longitudinal axis of the lid member.

A waste disposal system according to a third aspect of the invention includes a housing and a lid member that is hingedly mounted to the housing. The lid member has a longitudinal axis that is substantially vertical when the lid is in a closed position. A powder dispensing unit is mounted to an underside of the lid. The powder dispensing unit includes a container defining an interior space in which a powder may be stored, and a directional dispensing portion having a dispensing orifice for dispensing powder from the container into a targeted portion of the waste disposal unit. The dispensing orifice is positioned a first distance from the underside of the lid member, measured parallel to said longitudinal axis, that is within a range of about 3.0 cm to about 15.0 cm.

According to a fourth aspect of the invention, a waste disposal system includes a housing and a lid member that is movably mounted to the housing by a hinge. The lid has a longitudinal axis that is substantially vertical when the lid is in a closed position. A powder dispensing unit mounted to an underside of the lid. The powder dispensing unit includes a container defining an interior space in which a powder may be stored, and a directional dispensing portion for dispensing powder from the container into a targeted portion of the waste disposal unit. The directional dispensing portion is constructed and arranged to concentrate dispersal of the powder to a single side of the container that is away from the hinge.

A waste disposal system according to a fifth aspect of the invention includes a housing; a lid member movably mounted to the housing by a hinge, the lid having a longitudinal axis that is substantially vertical when said lid is in a closed position; and a powder dispensing unit mounted to an underside of the lid, the powder dispensing unit comprising a container defining an interior space in which a powder may be stored, and at least one dispensing orifice defined in the container, the container further having a recommended minimum fill level and a recommended maximum fill level, and wherein an internal volume of the container between the recommended minimum and maximum fill levels divided by the total cross-sectional area of said at least one dispensing orifice is substantially within a range of about 350 cm to about 5100 cm.

According to a sixth aspect of the invention, a waste disposal system includes a housing; a lid member movably mounted to the housing by a hinge, the lid having a longitudinal axis that is substantially vertical when the lid is in a closed position; and a powder dispensing unit mounted to an underside of the lid, the powder dispensing unit comprising a container defining an interior space in which a powder may be stored, and at least one dispensing orifice defined in the container, and wherein the container and the dispensing orifice are constructed and arranged to conserve powder material so as to ensure that powder material may be dispensed for a number of lid opening cycles that is substantially within a range of about 600 to about 2000.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

Figure 1:
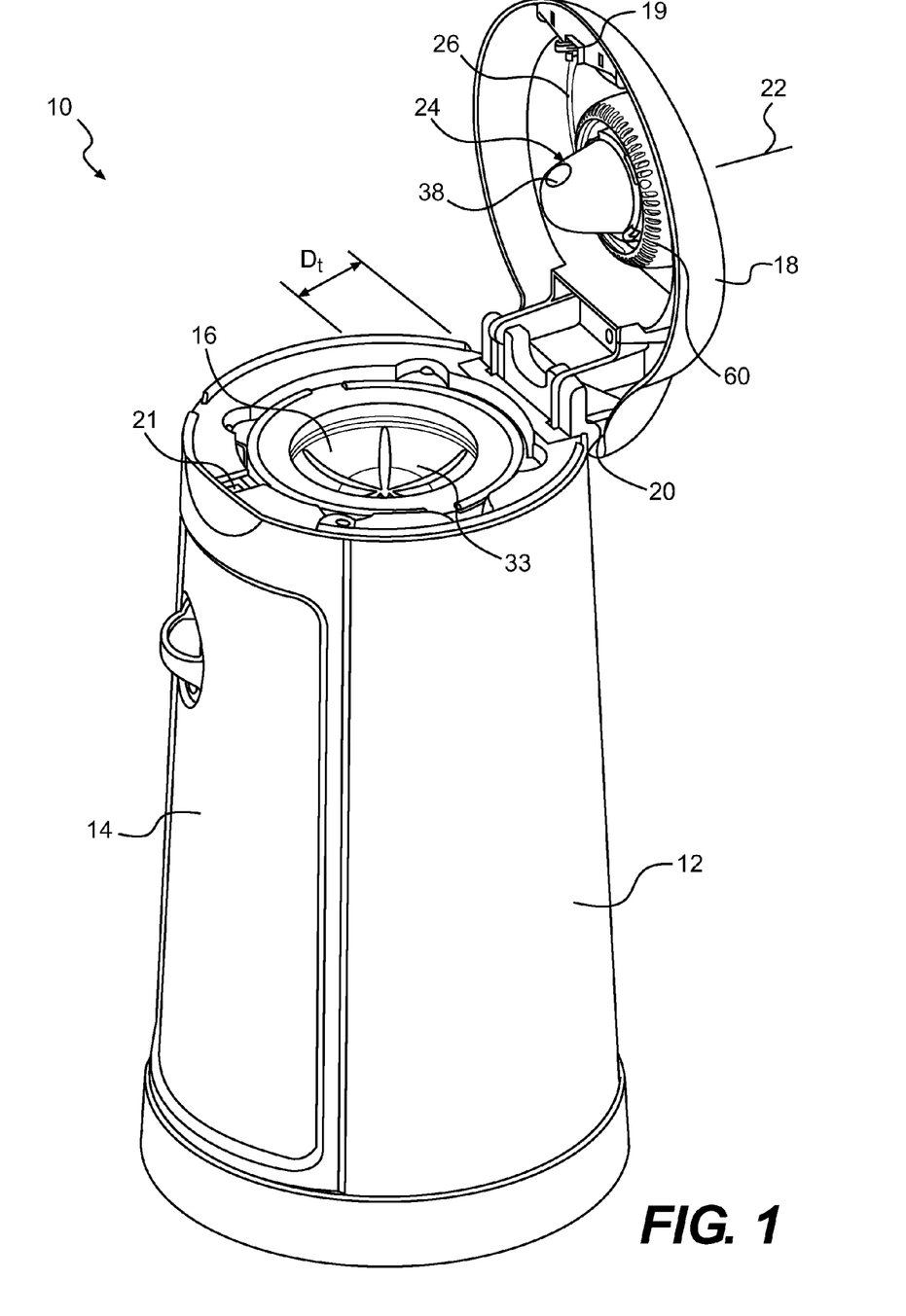
FIG. 1 is a perspective view of a waste disposal system that is constructed according to a preferred embodiment of the invention.
Figure 2:
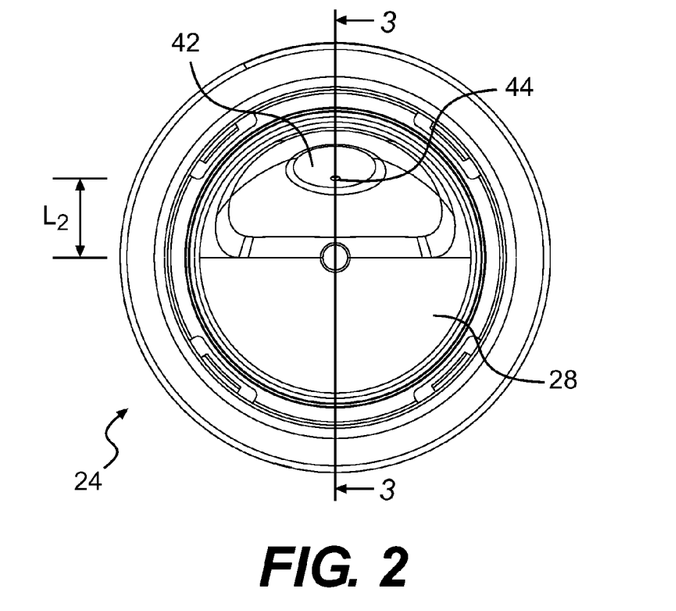
FIG. 2 is a bottom plan view of a powder dispensing unit that is constructed according to the preferred embodiment of the invention.

Referring now to the drawings, wherein like reference numerals designate corresponding structure throughout the views, and referring in particular to FIG. 1, a waste disposal system 10 according to a preferred embodiment of the invention includes a housing 12 defining an internal storage space that may be accessed by a parent or a caregiver through a hinged door 14. In the preferred embodiment, waste disposal system 10 is constructed as a diaper pail assembly that uses a modular bag assembly having a flexible, liquid and air impervious pleated bag having an attached foldable frame.

Waste disposal system 10 preferably includes a mechanism 16 for holding and twisting an intermediate portion of the flexible bag while the bag frame is held fixed by the housing. A lower portion of the flexible bag is positioned within the internal storage space for holding waste articles such as used disposable diapers. In alternative embodiments, the waste disposal system could be any type of waste container for residential, institutional or industrial use.

Referring again to FIG. 1, waste disposal system 10 further includes a lid member 18 that is movably mounted with respect to the housing 12 by a hinge mechanism 20. Lid member 18 defines a longitudinal axis 22 that is preferably oriented substantially vertically when the lid 18 is in the closed position. In the preferred embodiment, a releasable locking mechanism including a laterally expandable plunger 19 that is provided on the lid member 18 and a mating recess 21 that is defined within the housing 12 permits the lid member to be releasably locked in the closed position.

In order to open the waste disposal system 10 by lifting the lid member 18, the plunger 19 is moved and laterally contracted by an actuator button in order to disengage a latch portion 19 thereof from the mating recess 21. When the lid member 18 is pressed downwardly by a parent or caregiver in order to close the waste disposal system 10, the releasable locking mechanism engages with a slight hesitation and click as the laterally expandable latch portion 19 passes over the restriction of the recess 21 and temporarily laterally contracts against a spring bias, which is advantageous for facilitating powder distribution for reasons that are described in greater detail below.

Waste disposal system 10 further includes a powder dispensing unit 24 that is preferably releasably secured to an underside 26 of the lid member 18. Specifically, powder dispensing unit 24 is releasably secured to a mounting receptacle 60, described in further detail below, which in turn is mounted to the underside 26 of the lid member 18.

Figure 3:
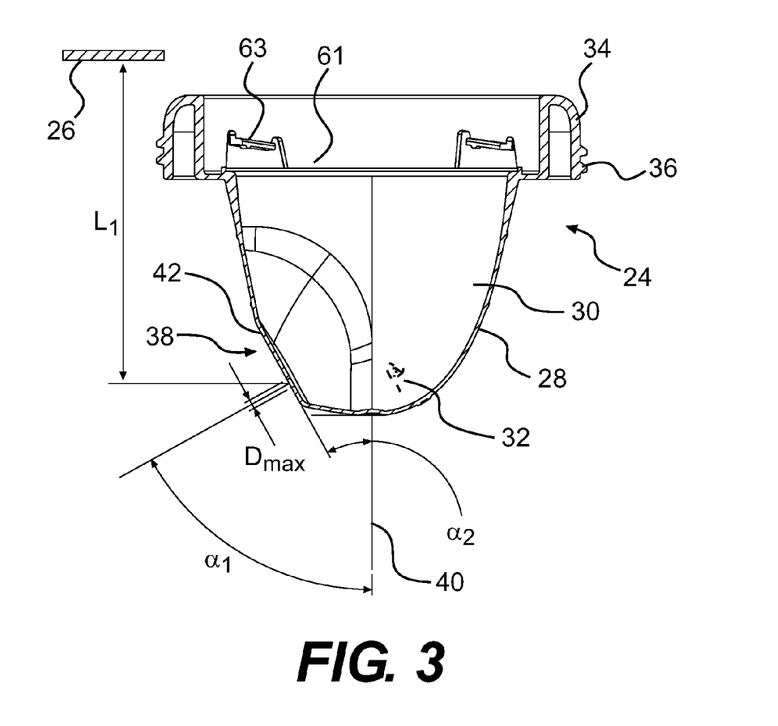
FIG. 3 is a side elevational view taken along lines 3-3 in FIG. 2.

Referring briefly to FIG. 3, it will be seen that the powder dispensing unit 24 preferably includes a container 28 that defines an interior space 30 in which a powder material 32 such as sodium bicarbonate may be stored. For purposes of this document, the term powder material includes any type of powdered or granular substance without regard to the degree of granularity. Any alternative odor-absorbing, odor masking or sanitizing powder could be used, as could a composite powder that has more than one of such properties. A sanitizing powder is a powder that has antibacterial or antiviral properties. Other powders such as talcum powder or baby powder could alternatively be used in the powder dispensing unit 24.

The powder material 32 preferably has a granularity that is expressed as a mean particle size maximum dimension that is substantially within a range of about 40 microns to about 140 microns, more preferably within a range of about 60 microns to about 120 microns and most preferably within a range of about 80 microns to about 100 microns. The material 32 also preferably has a bulk density that is substantially within a range of about 48 $lb/ft^3$ to about 78 $lb/ft^3$, more preferably within a range of about 53 $lb/ft^3$ to about 73 $lb/ft^3$ and most preferably within a range of about 58 $lb/ft^3$ to about 68 $lb/ft^3$.

Container 28 is preferably fabricated from a substantially rigid plastic material, which is preferably translucent, and more preferably transparent. In the preferred embodiment, container 28 includes an integral upper mounting flange 34 having external helical threading 36.

The container 28 also advantageously includes a directional dispensing portion 38 for dispensing powder material 32 from the container 28 into a targeted portion of the waste disposal unit 10. In the preferred embodiment, the targeted portion is a central portion 33 of the waste disposal system 10 that is substantially radially inward of the hinge mechanism 20 and that is substantially above a portion of the mechanism 16 for holding and twisting an intermediate portion of the flexible bag. More preferably, the targeted portion is above a portion of the flexible bag itself when it is positioned within the mechanism 16. The targeted portion preferably does not overlie any upper horizontal portion of the outer housing 12. The targeted portion is preferably positioned radially inward of the hinge mechanism by a distance $D_t$ that is at least substantially about 3 cm, more preferably at least substantially about 5 cm and most preferably at least substantially about 9 cm.

The directional dispensing portion 38 is constructed and arranged to concentrate and more preferably limit the initial dispersal of the powder material 32 as originating from a single side of the container 28, which is preferably a side of the container 28 that is away from the hinge mechanism 20. More preferably, the directional dispensing unit 38 is constructed and arranged to concentrate and limit the initial dispersal of the powder material 32 to a side of the container 28 that is substantially diametrically opposed to the hinge mechanism 20.

Preferably, the directional dispensing portion 38 is constructed and arranged to limit initial dispersal of the powder material 32 as it leaves the container 28 within an angular range $\alpha_1$ that is substantially about 40° to about 80° with respect to the longitudinal axis 40 of the container 28. In the preferred embodiment, the longitudinal axis 40 of the container 28 is substantially coincident with the longitudinal axis 22 of the lid member 18 when the lid member 18 is in the closed position. Accordingly, the directional dispensing portion 38 is also constructed and arranged to limit initial dispersal of the powder material 32 within an angular range $\alpha_1$ that is substantially about 40° to about 80° with respect to the longitudinal axis 22 of the lid member 18 when the lid member 18 is in the closed position.

More preferably, the angular range $\alpha_1$ is substantially about 45° to about 75°, and most preferably it is substantially about 50° to about 70°.

In the preferred embodiment, the directional dispensing portion 38 has a single dispensing orifice 44 that is defined in a substantially flat surface portion 42 that is located on one side of the container 28. Alternatively, multiple dispensing orifices could be provided on the substantially flat surface portion 42.

Orifice 44 preferably is substantially circular in cross-section, but it could alternatively be constructed to have a polygonal or oval shape. Dispensing orifice 44 preferably has a maximum diameter $D_{max}$ that is substantially within a range of about 0.5 mm to about 5.0 mm, that is more preferably within a range of substantially about 0.75 mm to about 3.5 mm and that is most preferably within a range of substantially about 1.0 mm to about 2.5 mm.

The substantially flat surface portion 42 is oriented so as to define an angle $\alpha_2$ with respect to the longitudinal axis 40 of the container 28. Angle $\alpha_2$ is preferably substantially within a range of substantially about 5.0 degrees to about 60.0 degrees. More preferably, angle $\alpha_2$ is substantially within a range of about 15.0 degrees to about 45.0 degrees, and is most preferably substantially within a range of about 20.0 degrees to about 40.0 degrees.

The dispensing orifice 44 is also preferably positioned at a first longitudinal distance $L_1$, measured axially in a direction that is parallel to the longitudinal axis 22 of the lid member 18, from the underside 26 of the lid member 18. Distance $L_1$ is preferably substantially within a range of about 3.0 cm to about 15.0 cm. More preferably, the first distance $L_1$ is substantially within a range of about 4.5 cm to about 8.5 cm, and most preferably it is substantially within a range of about 5.0 cm to about 7.0 cm.

Container 28 is moreover preferably constructed so that the dispensing orifice 44 is spaced a second lateral distance $L_2$ from the longitudinal axis 40 of the container 28. Second lateral distance $L_2$ is preferably substantially within a range of about 0.25 cm to about 6.0 cm. More preferably, distance $L_2$ is substantially within a range of about 0.5 cm to about 4.0 cm and most preferably it is substantially within a range of about 1.0 cm to about 2.5 cm.

Figure 4:
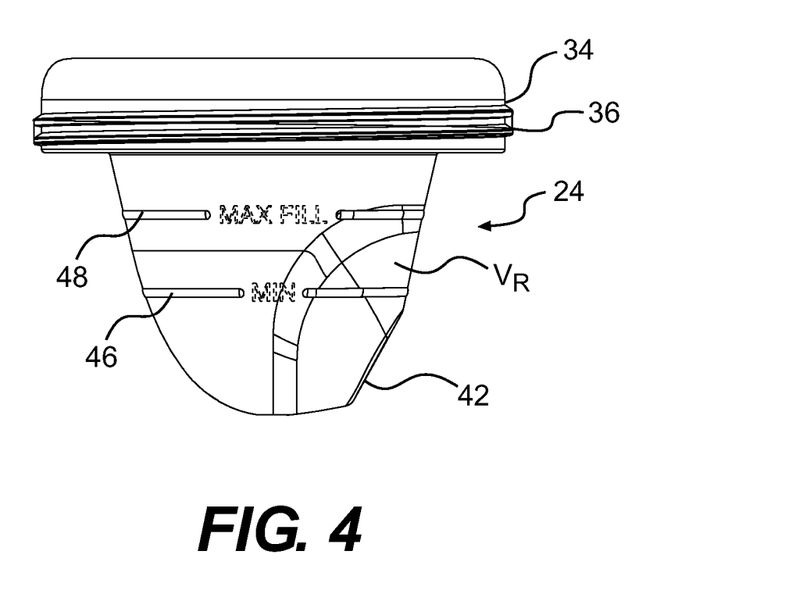
FIG. 4 is a side elevational view of the powder dispensing unit that is shown in FIG. 2.
Figure 5:
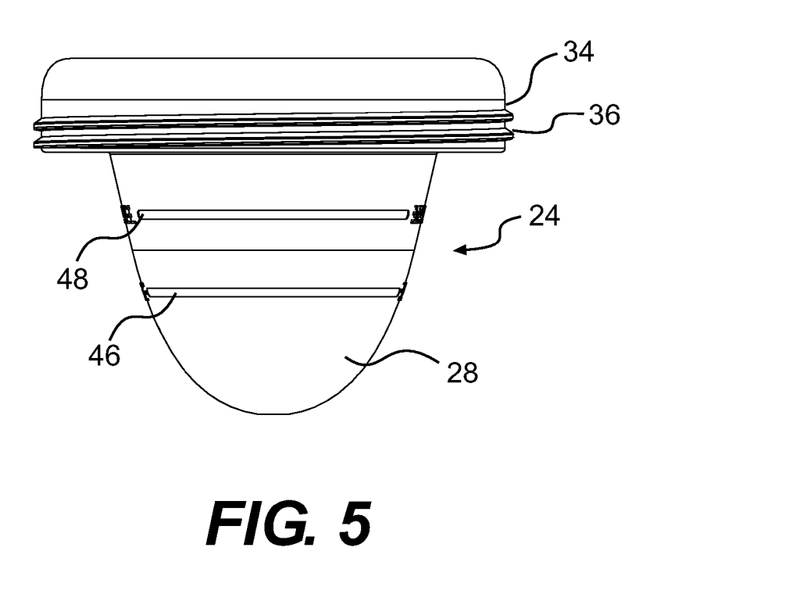
FIG. 5 is a rear elevational view of the powder dispensing unit that is shown in FIG. 2.

Referring briefly to FIG. 4, which is a side elevational view of the powder dispensing unit 24, it will be seen that the container 28 is preferably provided with first indicia 46 for indicating a recommended minimum fill level and second indicia 48 for indicating a recommended maximum fill level. Indicia 46, 48 provide guidance to a parent or caregiver as to the optimal fill level for the powder material 32 within the interior space 30 of the container 28. Preferably, the indicia 46, 48 are also visible from the rear side of the container 28, as is shown in FIG. 5. The indicia 46, 48 are preferably integrally molded into the container 28 using the same transparent material from which the rest of the container 28 is fabricated. Alternatively, the indicia 46, 48 could be formed from a translucent or opaque material, or it could be printed or silkscreened onto the container 28.

Preferably, container 28 is sized and shaped so as to have a first internal volume corresponding to the recommended minimum fill level that is preferably within a range of about 5 cm$^3$ to about 50 cm$^3$, that is more preferably within a range of about 7 cm$^3$ to about 40 cm$^3$, and that is most preferably within a range of about 10 cm$^3$ to about 30 cm$^3$.

Container 28 also preferably has a second internal volume corresponding to the recommended maximum fill level that is preferably within a range of about 15 cm$^3$ to about 120 cm$^3$, that is more preferably within a range of about 20 cm$^3$ to about 80 cm$^3$, and that is most preferably within a range of about 25 cm$^3$ to about 65 cm$^3$.

Container 28 further defines a third internal volume $V_R$, shown in FIG. 4, which is the internal space within the container 28 between the recommended minimum and maximum fill levels, that is preferably substantially within a range of about 10 cm$^3$ to about 70 cm$^3$, more preferably within a range of about 13 cm$^3$ to about 40 cm$^3$, and most preferably within a range of about 15 cm$^3$ to about 35 cm$^3$.

The container 28 is preferably fabricated from a material that will minimize the potential for any buildup of static electricity that could cause the powder material to clump or cling to the internal surface use of the container 28 or the dispensing orifice 44. Preferably, the internal surfaces of container 28 and the surfaces defining the dispensing orifice 44 are fabricated from a plastic material having anti-stick properties such as polypropylene. In the preferred embodiment, the entire container 28, including the internal surfaces and the surfaces defining the dispensing orifice 44, is fabricated from a polypropylene Random Copolymer such as YUNGSOX® PP 5090T, commercially available from Formosa Plastics Corporation in Taiwan.

A material that has anti-static or static dissipative properties may be used, such as a material having a resistivity that is substantially within a range of about $10^7$ to about $10^{12}$ ohms/cm$^2$. Alternatively, a material that is conductive could be used to control potential static charges, such as a material having a resistivity that is substantially within a range of about $10^3$ to about $10^6$ ohms/cm$^2$.

The container 28 is further preferably constructed and arranged in such a manner that the powder material 32 within the third internal volume between the recommended minimum and maximum fill levels will be dispensed at a rate per each cycle of opening and closing of the lid member 18 that ensures that the container 28 has sufficient capacity to effectively dispense an amount of powder between refills that substantially correlates with the anticipated lifespan of the effective odor absorbing capability of the powder material 32. Container 28 is also constructed and arranged to ensure that an amount of powder material 32 is dispensed per each lid opening cycle that provides effective odor absorbing or deodorizing capability within each lid opening cycle.

Preferably, the directional dispensing system 38 is constructed so that the powder material 32 within the third internal volume is conserved to be dispensed substantially within a range of about 600 to about 2000 lid opening cycles. More preferably, directional dispensing system 38 is constructed so that the powder material 32 within the third internal volume is conserved to be dispensed substantially within a range of about 750 to about 1600 lid opening cycles, and most preferably substantially within a range of about 900 to about 1200 lid opening cycles.

One physical characteristic of the directional dispensing system 38 that is important in ensuring that the powder material 32 is conserved for the anticipated number of lid opening cycles is the relationship between the internal volume of the container 28 and the cross-sectional area of the dispensing orifice 44. Preferably, the third internal volume divided by the cross-sectional area of the dispensing orifice 44 is substantially within a range of about 350 cm to about 5100 cm, more preferably within a range of about of about 500 cm to about 3000 cm, and most preferably within a range of about 700 cm to about 1500 cm.

Figure 6:
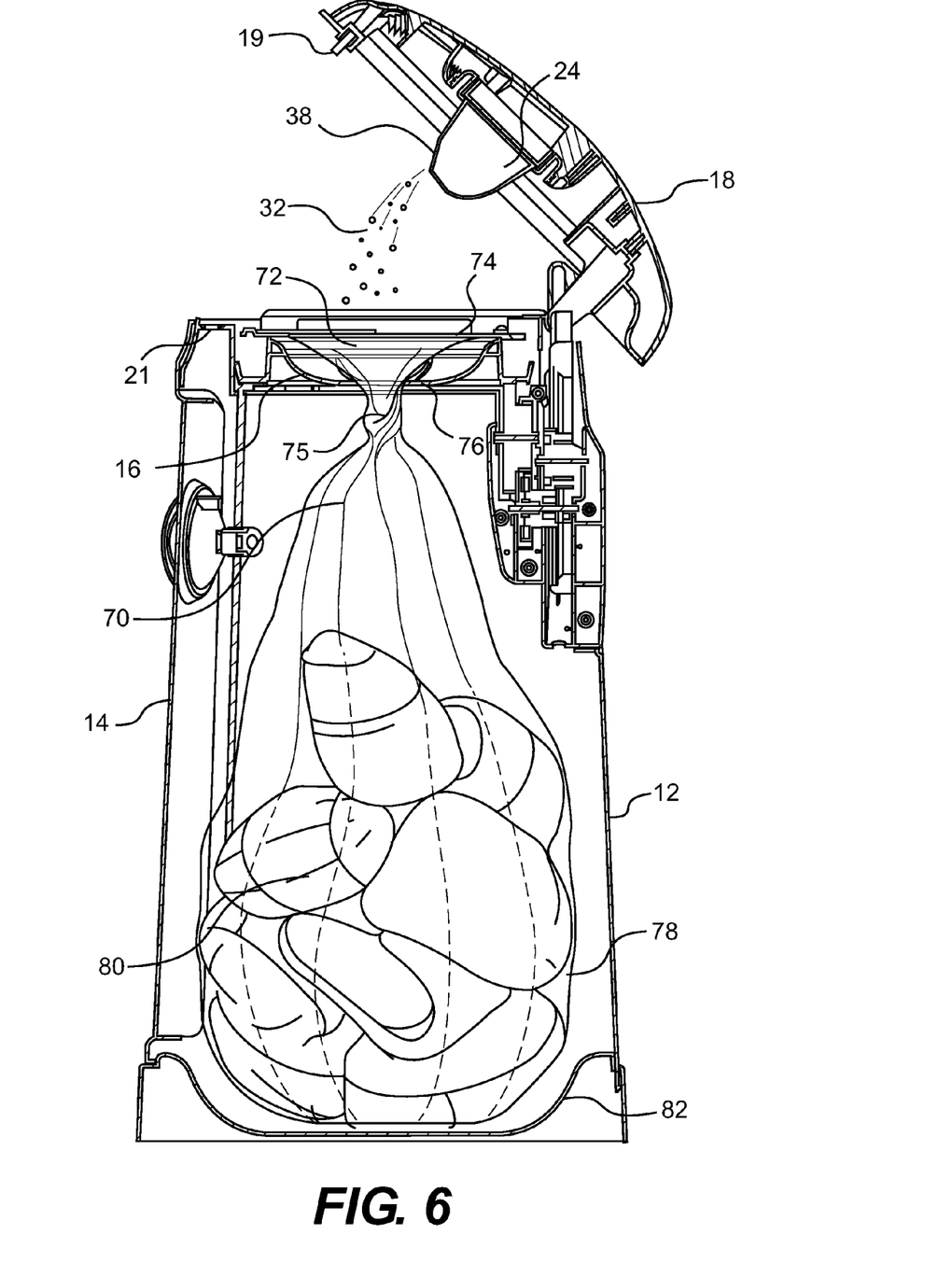
FIG. 6 is a diagrammatical depiction of the powder dispensing unit that is shown in FIG. 2 in use.

FIG. 6 is a diagrammatical view showing the powder dispensing unit 24 in the process of dispensing a powder material 32 into a waste disposal system that is constructed according to the preferred embodiment of the invention. It is readily apparent from viewing FIG. 6 how the directional dispensing portion 38 helps to direct the powder material toward the center of the waste disposal system 10 when the lid member 18 is partially open.

In the preferred embodiment, the waste disposal system 10 is a diaper pail assembly in which a flexible plastic bag 70 having an upper portion 72 that is mounted to a bag frame 74 is mounted within the system 10 so that the bag frame 74 is rotationally fixed with respect to the housing 12. The bag frame 74, which has a central opening defined therein, is mounted directly beneath the powder dispensing unit 24. It is important that powder material that is dispensed from the powder dispensing unit 24 falls into the central opening of the bag frame 74 and not into other areas near the top of the housing 12. The directional dispensing portion 38 facilitates this.

In the preferred embodiment, a plurality of inwardly radially extending resilient fingers 76 engage and twist an outer surface of an intermediate portion of the flexible bag 70 in order to create a twisted intermediate portion 75 of the flexible bag 70 in order to form an odor seal while the upper portion 72 and a lower portion 78 remain substantially stationary. The lower portion 78 of the flexible bag 70 is shown in FIG. 6 to be holding a number of waste packages 80, which may be used disposable diapers. The consumer will insert the waste packages 80 through the central opening of the bag frame 74 and downwardly through the twisted portion 75 of the bag 70 into the lower portion 78. An odor seal is maintained between the twisted portion and the outer surface of the waste package 80 as it is being pushed through the twisted portion.

Accordingly, powder material 32, after falling into the upper portion 72 of the flexible bag 70, is retained in the upper portion 72 above the twisted intermediate portion 75 of the flexible bag 70 for a period of time before a portion of it is swept by the parent or caregiver into the lower portion 78 of the flexible bag as the parent of caregiver pushes a waste package 80 downwardly through the twisted portion 75. The powder material 32 accordingly deodorizes or absorbs odor in the upper area of the diaper pail assembly 10 for a period of time when it is positioned within the upper portion 72 of the flexible bag 70, and later in the lower portion 78 of the flexible bag 70.

A bottom surface 82 of the housing 12 is concavely curved in order to center and align the flexible bag 70 in order to optimize the space and provide longitudinal alignment of the flexible bag 70 with respect to the pail and the mechanism 16.

Figure 9:
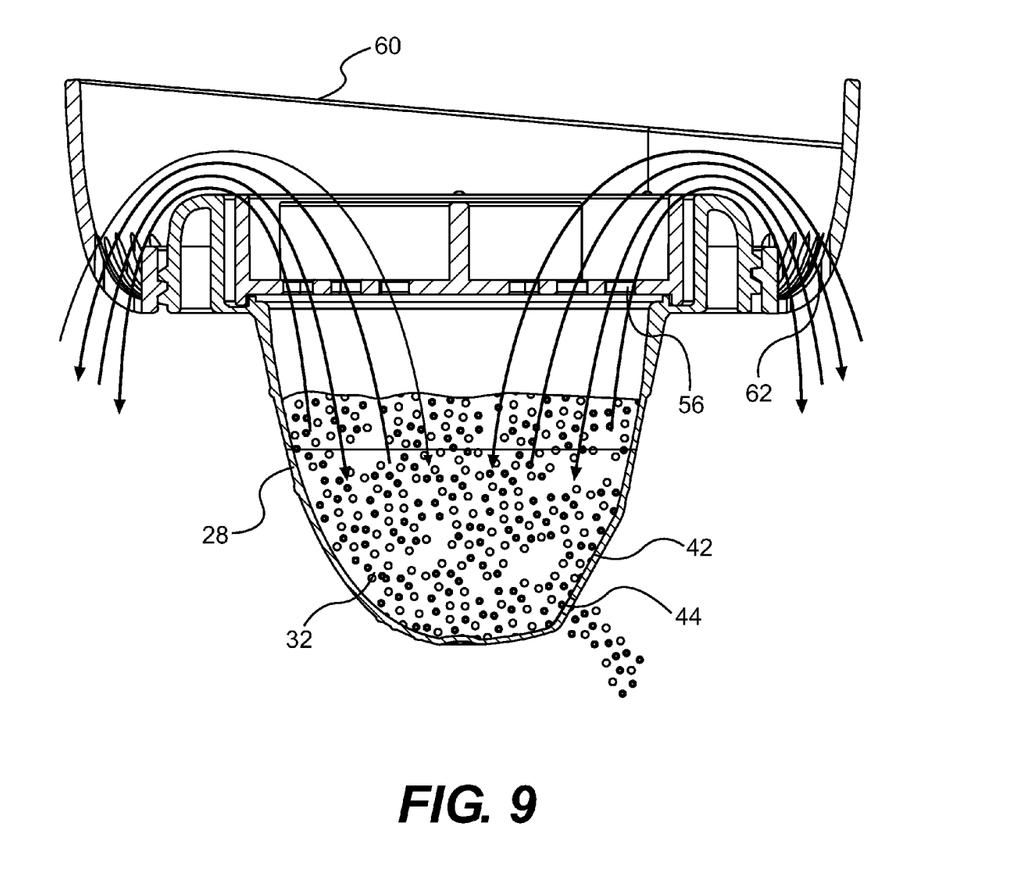
FIG. 9 is a diagrammatical depiction depicting venting of the waste disposal system shown in FIG. 1.

In the preferred embodiment, the powder dispensing unit 24 is constructed and arranged to dispense a powdered deodorant or odor absorbing substance such as sodium bicarbonate directly into the interior of the waste disposal system 10. In addition, it is constructed to facilitate and permit air within the waste disposal system 10 to contact and potentially circulate past the powder material, including when the lid member 18 is closed, in order to reduce objectionable odors within the waste disposal system 10. This is achieved by means of a venting path that is defined in the powder dispensing unit 24, which is shown diagrammatically in FIG. 9. Opening and closing of the lid member 18 further facilitates circulation of air through the venting path.

Figure 7:
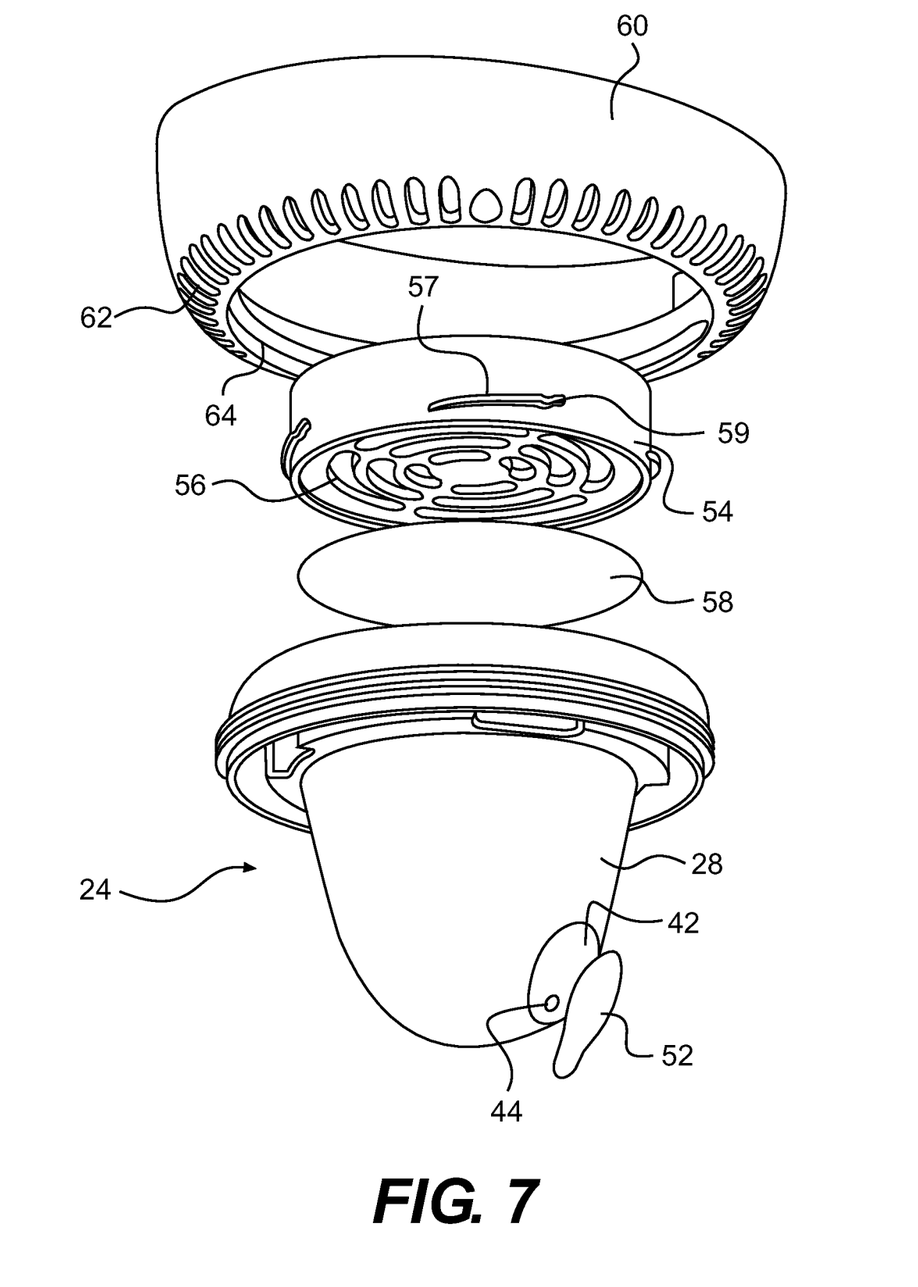
FIG. 7 is a perspective exploded view of the powder dispensing unit that is shown in FIG. 2.

FIG. 7 is an exploded perspective view depicting the preferred components of the powder dispensing unit 24. In addition to the container 28, the powder dispensing unit 24 includes a removable cover 54 that has at least one vent opening 56 defined therein and a porous membrane 58 that is positioned between the removable cover 54 and a container 28 so as to be interposed within the vent opening 56.

In the preferred embodiment, vent opening 56 is embodied as a plurality of substantially concentric, curved individual vent openings, each of which preferably has a substantially constant radius of curvature as view in top plan. All of the individual vent openings preferably have a common center point of curvature, which is preferably in the center of the removable cover 54 and substantially coincident with the longitudinal axis 40 of the container 28. However, the vent opening 56 could be sized and shaped in any one of a number of possible different ways.

The removable cover 54 is releasably secured during use within a recessed upper inner seating surface 61 of the container 28, best shown in FIG. 3, by means of engagement of at least one helical thread 57 that is provided on an outer circumferential surface of the cover 54 with a mating internal thread 63 that is provided on the recessed upper inner seating surface 61. Structure 59 such as a thread stop is also preferably provided for limiting the maximum amount of rotation that is permitted between the removable cover 54 and the container 28. Alternatively, any other mechanical structure for attaching the removable cover 54 to the container 28 could be provided, including but not limited to a tab lock arrangement, a snap arrangement or a latching arrangement.

Preferably, the porous membrane 58 includes a fibrous matrix that may be bound together using a binder material such as latex, and which can include natural and/or synthetic fibers. Preferably the porous membrane has an air permeability as measured by the "Frazier Number" (also referred to in the industry as "CFM") that is substantially within a range of about 15 to about 500, and that is more preferably within a range of about 30 to about 380 at a differential pressure of 0.5 inches of water. Most preferably, porous membrane 58 has a Frazier Number that is substantially within a range of about 40 to about 410 at a differential pressure of 0.5 inches of water. The Frazier Number/CFM rating is a measurement of air flow in cubic feet per square foot of sample area per minute at a given differential pressure.

Porous membrane 58 may also be fabricated from a material that has anti-static or static dissipative properties, such as a material having a resistivity that is substantially within a range of about $10^7$ to about $10^{12}$ ohms/cm$^2$. Alternatively, a material that is conductive could be used to control potential static charges, such as a material having a resistivity that is substantially within a range of about $10^3$ to about $10^6$ ohms/cm$^2$.

Figure 8:
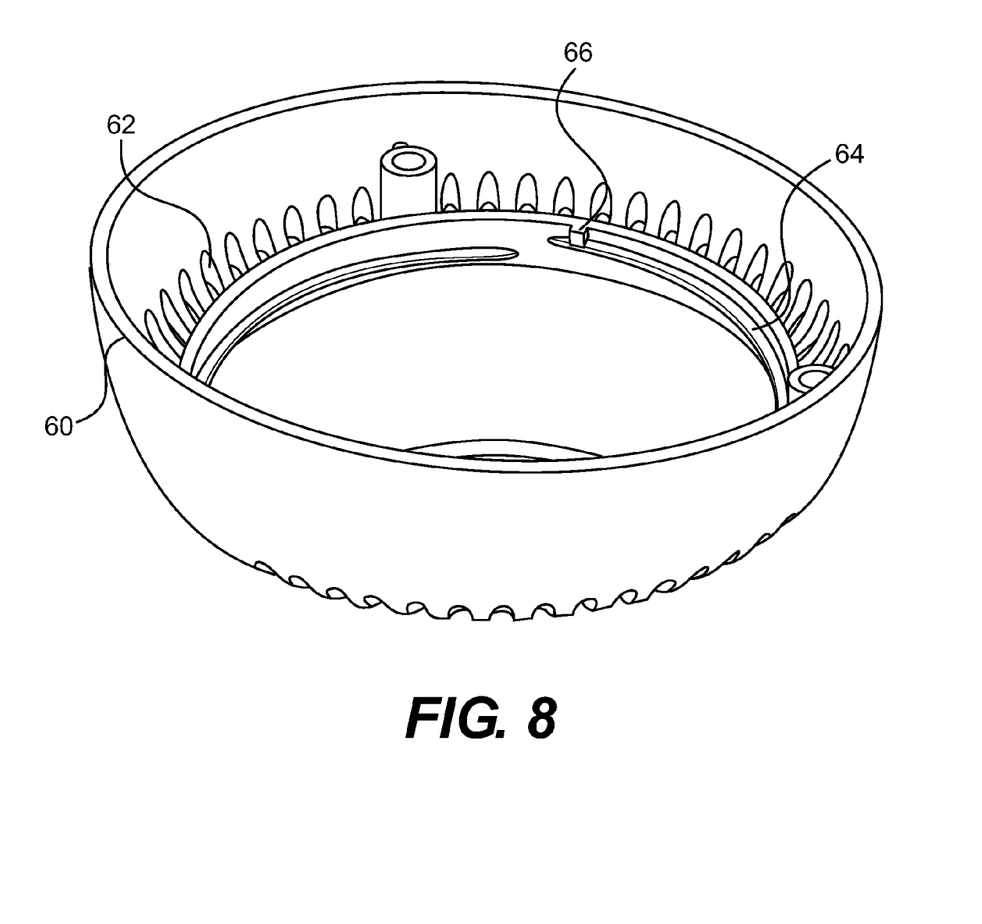
FIG. 8 is a fragmentary perspective view of a mounting receptacle that is part of the waste disposal system shown in FIG. 1.

In the illustrated embodiment, a mounting receptacle 60 is secured to the underside 26 of the lid member 18. The mounting receptacle 60 includes a central opening for receiving the mounting flange 34 of the container 28 and is provided with one or more internal helical threads 64 that are constructed and arranged to mate with the external helical threads 36 that are provided on the mounting flange 34 of the container 28. As is best shown in FIG. 8, rotation limiting and alignment structure such as a thread stop 66 is provided for limiting the maximum amount of rotation that is permitted to occur between the container 28 and a mounting receptacle 60. This will prevent overtightening of the container 28 within the mounting receptacle 60 as well as ensure the alignment of the directional dispensing portion 38 in opposition to the position of the hinge mechanism 20.

The powder dispensing unit 24 may be provided to the consumer both together with the initial sale of the waste disposal system 10 and as a separate modular refill product. The unit 24 may be packaged using a shrink wrapping technology to preserve the freshness of the powder 32, or a temporary adhesive barrier may be placed over the upper surface of the container 28 with the removable cover 54 in place in order to prevent air from circulating through the vent openings 56 and reducing the odor absorbing or masking capacity of the powder 32 before the unit 24 is used by the consumer.

The consumer will remove the packaging or the adhesive barrier prior to use. The consumer will then install the powder dispensing unit into the waste disposal system 10 by grasping the container 28 and causing the external threading 36 of the mounting flange 34 to mate with the internal threading 64 of the mounting receptacle 60 that is provided on the underside 26 of the lid member 18. An adhesive label 52 that is preferably provided on the flat surface 42 in order to seal the dispensing orifice 44 during transit and storage will then be removed by the consumer.

During normal use of the waste disposal system 10, air that is internal to the waste disposal system 10 is permitted to circulate and contact the odor absorbing or deodorizing powder 32 within the container 28 by flowing through the venting path that includes the vent openings 62 that are defined in the mounting receptacle 60 and the vent openings 56 that are defined in the removable cover 54. Because the venting path is located near the top of the waste disposal system 10, circulation of air therethrough may be aided by convection.

The outer absorbing or deodorizing powder material 32 may also be dispensed directly into the central portion 33 of the waste disposal system 10 as a result of the motion of the lid member 18 when it is opened and closed, or as a result of the parent or caregiver tapping on the lid member 18 or directly on the container 28. In addition, the latching mechanism 19, 21 of the waste disposal system 10 is constructed and arranged to create a slight hesitation that includes an initial deceleration and then a rapid acceleration into the closed position that has a tendency to cause some of the powder material 32 to be shaken out of the dispensing orifice 44 at the moment that closure of the lid member 18 is completed.

The parent or caregiver may directly access the interior space 30 of the container 28 by unscrewing the container 28 from the mounting receptacle 60 and then unscrewing the removable cover 54 from the container 28. At this point, he or she may add additional powder material into the interior space 30 of the container 28 in order to maintain the level of powder material 30 within the suggested limits that are communicated by the indicia 46, 48. The consumer may also change the odor-absorbing powder if he or she feels that its odor-absorbing capacity has been diminished.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A waste disposal system, comprising:
    a housing;
    a lid member hingedly mounted to said housing, said lid having a longitudinal axis that is substantially vertical when said lid is in a closed position; and
    a powder dispensing unit mounted to an underside of said lid, said powder dispensing unit comprising a container defining an interior space in which a powder may be stored, and a directional dispensing portion having a dispensing orifice for dispensing powder from the container into a targeted portion of the waste disposal system, and wherein said dispensing orifice is positioned a first distance from the underside of the lid member, measured parallel to said longitudinal axis, that is within a range of about 3.0 cm to about 15.0 cm.

2. A waste disposal system according to claim 1, wherein said first distance is within a range of about 4.5 cm to about 8.5 cm.

3. A waste disposal system according to claim 2, wherein said first distance is within a range of about 5.0 cm to about 7.0 cm.

4. A waste disposal system according to claim 1, wherein said dispensing orifice is further positioned a lateral distance from the longitudinal axis that is within a range of about 0.25 cm to about 6.0 cm.

5. A waste disposal system according to claim 4, wherein said lateral distance is within a range of about 0.75 cm to about 4.0 cm.

6. A waste disposal system according to claim 5, wherein said lateral distance is within a range of about 1.0 cm to about 2.5 cm.

7. A waste disposal system according to claim 1, wherein said directional dispensing portion is constructed and arranged to concentrate initial dispersal of the powder to a single side of the container.

8. A waste disposal system according to claim 7, wherein said single side of the container is away from said hinge.

9. A waste disposal system according to claim 8, wherein said single side of the container is substantially opposed to a side of the container bearing the hinge.

10. A waste disposal system according to claim 1, wherein said directional dispensing portion is constructed and arranged to concentrate dispersal of the powder to a single side of the container and within an angular range of about 45 degrees to about 75 degrees with respect to the longitudinal axis.

11. A waste disposal system according to claim 10, wherein said directional dispensing portion is constructed and arranged to concentrate dispersal of the powder to a single side of the container and within an angular range of about 50 degrees to about 70 degrees with respect to the longitudinal axis.

12. A waste disposal system according to claim 1, wherein said directional dispensing portion has a single dispensing orifice.

13. A waste disposal system according to claim 1, further comprising a venting path defined in said container, said venting path being in communication with said interior space for permitting air circulating within the waste disposal unit to contact powder within the container.

14. A waste disposal system according to claim 13, further comprising a porous membrane interposed within said venting path.

15. A waste disposal system according to claim 14, wherein said porous membrane has a Frazier Number permeability to air that is substantially within a range of about 15 to about 500 at a differential pressure of 0.5 inches of water.

16. A waste disposal system according to claim 1, further comprising a removable lid for permitting a consumer to access said interior space.

17. A waste disposal system according to claim 16, further comprising a venting path defined in said removable lid, said venting path being in communication with said interior space for permitting air circulating within the waste disposal unit to contact powder within the container.

18. A waste disposal system according to claim 16, wherein said removable lid is threadingly engaged with said container.

19. A waste disposal system according to claim 16, wherein further comprising a mounting portion having a helical thread on said removable lid, and further comprising a stop portion for limiting rotation of said removable lid with respect to the container.

20. A waste disposal system according to claim 1, further comprising a mounting assembly for releasably mounting the powder dispensing unit to the underside of said lid, said mounting assembly comprising at least one helical thread and a stop member for limiting rotation of the powder dispensing unit with respect to the underside of said lid.

21. A waste disposal system according to claim 1, further comprising a powder disposed in said interior space.

22. A powder dispenser according to claim 1, wherein said targeted portion of the waste disposal system is away from said hinge.

23. A powder dispenser according to claim 22, wherein said targeted portion of the waste disposal system is substantially opposed to said hinge.

24. A waste disposal system, comprising:
a housing;
a lid member movably mounted to said housing by a hinge, said lid having a longitudinal axis that is substantially vertical when said lid is in a closed position; and
a powder dispensing unit mounted to an underside of said lid, said powder dispensing unit comprising a container defining an interior space in which a powder may be stored, and a directional dispensing portion for dispensing powder from the container into a targeted portion of the waste disposal system, said directional dispensing portion being constructed and arranged to concentrate dispersal of the powder to a single side of the container that is away from said hinge.

25. A waste disposal system according to claim 24, wherein said directional dispensing portion is constructed and arranged to limit dispersal of the powder to a single side of the container that is substantially opposed to said hinge.

* * * * *